US007085652B2

(12) United States Patent  
Scaf et al.

(10) Patent No.: US 7,085,652 B2  
(45) Date of Patent: Aug. 1, 2006

(54) METHODS FOR SEARCHING POLYNUCLEOTIDE PROBE TARGETS IN DATABASES

(75) Inventors: Charles R. Scaf, San Francisco, CA (US); Nicolas Peyret, Foster City, CA (US); Francisco M. De La Vega, San Mateo, CA (US); Ryan T. Koehler, Hayward, CA (US); Eugene G. Spier, Palo Alto, CA (US)

(73) Assignee: Applera Corporation, Foster City, CA (US)

( * ) Notice: Subject to any disclaimer, the term of this patent is extended or adjusted under 35 U.S.C. 154(b) by 535 days.

(21) Appl. No.: 10/366,977

(22) Filed: Feb. 14, 2003

(65) Prior Publication Data

US 2003/0228591 A1 Dec. 11, 2003

Related U.S. Application Data

(60) Provisional application No. 60/357,548, filed on Feb. 15, 2002.

(51) Int. Cl.
G06F 19/00 (2006.01)
C12Q 1/68 (2006.01)

(52) U.S. Cl. ............................................. 702/20; 435/6
(58) Field of Classification Search ...................... None
See application file for complete search history.

(56) References Cited

OTHER PUBLICATIONS

Kaderali et al. Selecting signature oligonucleotides to identify organisms using DNA arrays. Bioinformatics vol. 18, No. 10, pp. 1340-1349 (2002).*
Hyndman et al. Software to Determine Optimal Oligonucleotide Sequences Based on Hybridization Simulation Data. BioTechniques, 1996, vol. 20, No. 6, pp. 1090-1097, especially p. 1090.
PCT International Search Report, mailed Aug. 15, 2003. For International Application No. PCT/US03/04354.
Lockhart, D.J.; et al., "Expression Monitoring by Hybridization to High-Density Oligonucleotide Arrays." Nature Biotechnology, vol. 14, (1996): pp. 1675-1680.
Myers, G. "A Fast Bit-Vector Algorithm for Approximate String Matching Based on Dynamic Programming." Journal of the ACM vol. 46, No. 3, (1999): pp. 395-415.
Peyret, N., and SantaLucia, J., Jr. "Prediction of Nucleic Acid Hybridization: Parameters and Algorithms." Abstract of Dissertation, Wayne State University, Detroit, MI: pp. 353-354.
Gotoh, O., "An Improved Algorithm For Matching Biological Sequences." J. Mol Biol. vol. 162, (1982): pp. 705-708.
Altschul, S.F., Gish, W., Miller, W., Myers, E.W., and Lipman, D.J. "Basic Local Alignment Search Tool." J. Mol. Biol., vol. 215, (1990): pp. 403-410.

Smith, T.F. and Waterman, M.S. "Identification of Common Molecular Subsequences." J. Mol. Biol., vol. 147, (1981): pp. 195-197.
Pearson, W.R., and Lipman, D.J. "Improved Tools for Biological Sequence Comparison." Proc. Nat'l. Acad. Sci. USA, vol. 85, (1988): pp. 2444-2448.
Peterson, J.C., et al., "Sequence Information Signal Processor for Local and Global String Comparisons," California Institute of Technology, Pasadena, CA, USA: U.S. Appl. No. 5,632,041 (1997).
Cherry, J.M., et al, SGD: Saccharomyces Genome Database. Nucleic Acids Res., vol. 26, (1998), No. 1; pp. 73-79.
Kane, M.D. et al., "Assessment of Sensitivity and Specificity of Oligonucleotide (50mer) Microarrays." Nucleic Acids Research,•vol. 28, No. 22, (2000): pp. 4552-4557.
Altschul, S.F., Madden, T.L., Schaffer, A.A., Zhang, J., Zhang, Z., Miller, W., and Lipman, D.J. "Gapped BLAST and PSI-BLAST: A New Generation of Protein Database Search Programs." Nucleic Acids Research, vol. 25, No. 17. (1997): pp. 3389-3402.
Lockhart, D.J., and Winzeler, E.A. "Genomics, Gene Expression and DNA Arrays." Nature vol. 405, (2000): pp. 827-836.
Roses, A. "Pharmacogenetics and the Practice of Medicine." Nature, vol. 405, (2000): pp. 857-865.
Duggan, D.J. et al., "Expression Profiling Using cDNA Microarrays." Nature Genetics Supplement, vol. 21, (1999): pp. 10-14.
Gray, D.M., and Tinoco, I. , Jr. "A New Approach to the Study of Sequence Dependent Properties of Polynucleotides." Biopolymers, vol. 9, (1970): pp. 223-244.
Allawi, H.T. and SantaLucia, J., Jr. "Thermodynamics and NMR of Internal G•T Mismatches in DNA." Biochemistry, vol. 36, (1997): pp. 10581-10594.
Allawi, H.T. and SantaLucia, J., Jr. "Nearest Neighbor Thermodynamic Parameters for Internal G•A Mismatches in DNA." Biochemistry, vol. 37, (1998): pp. 2170-2179.
Allawi, H.T. and SantaLucia, J., Jr. "Thermodynamics of Internal C•T Mismatches in DNA." Nucleic Acids Research, vol. 26, No. 11, (1998): pp. 2694-2701.
Allawi, H.T. and SantaLucia, J., Jr. "Nearest Neighbor Thermodynamics of Internal A•C Mismatches in DNA: Sequence Dependence and pH Effects." Biochemistry, vol. 37, (1998): pp. 9435-9444.

(Continued)

*Primary Examiner*—John S. Brusca
(74) *Attorney, Agent, or Firm*—Harness, Dickey & Pierce, P.L.C.

(57) ABSTRACT

Methods for determining the binding affinity of a probe to a target or targets in a polynucleotide composite using an automated system. Such methods determine relative binding sites based on thermodynamic principles, using a thermodynamic alphabet and a thermodynamic scoring matrix, with appropriate computer software, such as BLASTP. The invention also provides methods for designing polynucleotide probes to be used in hybridization assays, and minimizing the occurrence of cross-hybridization.

27 Claims, 4 Drawing Sheets

OTHER PUBLICATIONS

Peyret, N., et al., "Nearest Neighbor Thermodynamics and NMR of DNA Sequences with Internal A•A, C•C, G•G, and T•T Mismatches." Biochemistry, vol. 38, (1999): pp. 3468-3477.

SantaLucia, J., Jr. "A Unified View of Polymer, Dumbbell, and Oligonucleotide DNA Nearest-Neighbor Thermodynamics." Proc. Nat'l. Acad. Sci. USA, vol. 95, (1998): pp. 1460-1465.

Li, Fugen and Stormo, Gary D. "Selecting Optimum DNA Oligos for Microarrays." 2000 IEEE: pp. 200-207.

Ahsen, Nicholas von, et al. "Application of a Thermodynamic Nearest-Neighbor Model to Estimate Nucleic Acid Stability and Optimize Probe Design: Prediction of Melting Points of Multiple Mutations of Apolipoprotein B-3500 and Factor V with a Hybridization Probe Genotyping Assay on the LightCycler.", Clinical Chemistry—von Ahsen et al. 45 (12): 2094: pp. 1-13, 1999.

Rognes, T., and Seeberg, E. "Six Fold Speed-up of Smith-Waterman Sequence Database Searches Using Parallel Processing on Common Microprocessors." Bioinformatics vol. 16, No. 8., (2000), pp. 699-706.

Dayhoff, M. O., Schwartz, R. M., and Orcutt, B. C., "A Model of Evolutionary Change in Proteins." Atlas of Protein Sequence and Structure, 1978, pp. 345-352.

Henikoff, S., and Henikoff, J. G. "Amino Acid Substitutions Matrices From Protein Blocks." (1992) Proc. Natl. Acad. Sci. USA, vol. 89, pp. 10915-10919.

* cited by examiner

```
                         SEQUENCE LISTING

<160> NUMBER OF SEQ ID NOS: 8

<210> SEQ ID NO 1
<211> LENGTH: 23
<212> TYPE: DNA
<213> ORGANISM: Unknown
<220> FEATURE:
<223> OTHER INFORMATION: Generic DNA sequence not pertaining to a
      specific organism
<220> FEATURE:
<221> NAME/KEY: misc_binding
<222> LOCATION: (1)..(23)
<223> OTHER INFORMATION:

<400> SEQUENCE: 1
ctgcctgtcc caatgctcha gcc                                              23

<210> SEQ ID NO 2
<211> LENGTH: 23
<212> TYPE: DNA
<213> ORGANISM: unknown
<220> FEATURE:
<223> OTHER INFORMATION: Generic DNA sequence not pertaining to a
      specific organism
<220> FEATURE:
<221> NAME/KEY: misc_binding
<222> LOCATION: (1)..(23)
<223> OTHER INFORMATION:

<400> SEQUENCE: 2
ctgcctgtcc cvvtgctcca gcc                                              23

<210> SEQ ID NO 3
<211> LENGTH: 24
<212> TYPE: DNA
<213> ORGANISM: unknown
<220> FEATURE:
<223> OTHER INFORMATION: Generic DNA sequence not pertaining to a
      specific organism
<220> FEATURE:
<221> NAME/KEY: misc_binding
<222> LOCATION: (1)..(24)
<223> OTHER INFORMATION:

<400> SEQUENCE: 3
ctgcctgtcc caatgctcha gccc                                             24
```

```
<210> SEQ ID NO 4
<211> LENGTH: 24
<212> TYPE: DNA
<213> ORGANISM: Unknown
<220> FEATURE:
<223> OTHER INFORMATION: Generic DNA sequence not pertaining to a
      specific organism
<220> FEATURE:
<221> NAME/KEY: misc_binding
<222> LOCATION: (1)..(24)
<223> OTHER INFORMATION:

<400> SEQUENCE: 4
ctgcctgtcc ctctgctccg gccc                                          24

<210> SEQ ID NO 5
<211> LENGTH: 25
<212> TYPE: DNA
<213> ORGANISM: Unknown
<220> FEATURE:
<223> OTHER INFORMATION: Generic DNA sequence not pertaining to a
      specific organism
<220> FEATURE:
<221> NAME/KEY: misc_binding
<222> LOCATION: (1)..(25)
<223> OTHER INFORMATION:

<400> SEQUENCE: 5
attgtgctga gtagcttagc tagcg                                         25

<210> SEQ ID NO 6
<211> LENGTH: 25
<212> TYPE: DNA
<213> ORGANISM: Unknown
<220> FEATURE:
<223> OTHER INFORMATION: Generic DNA sequence not pertaining to a
      specific organism
<220> FEATURE:
<221> NAME/KEY: misc_binding
<222> LOCATION: (1)..(25)
<223> OTHER INFORMATION:

<400> SEQUENCE: 6
cgctagctaa gctactcagc acaat                                         25

<210> SEQ ID NO 7
<211> LENGTH: 14
<212> TYPE: DNA
<213> ORGANISM: Unknown
<220> FEATURE:
<223> OTHER INFORMATION: Generic DNA sequence not pertaining to a
      specific organism
<220> FEATURE:
<221> NAME/KEY: misc_binding
<222> LOCATION: (1)..(14)
<223> OTHER INFORMATION:

<400> SEQUENCE: 7
gctaagctac tcag                                                     14

<210> SEQ ID NO 8
<211> LENGTH: 14
<212> TYPE: DNA
<213> ORGANISM: Unknown
<220> FEATURE:
<223> OTHER INFORMATION: Generic DNA sequence not pertaining to a
      specific organism
```

-continued

```
<220> FEATURE:
<221> NAME/KEY: misc_binding
<222> LOCATION: (1)..(14)
<223> OTHER INFORMATION:

<400> SEQUENCE: 8
gctaagctac tcag                                                      14
```

METHODS FOR SEARCHING POLYNUCLEOTIDE PROBE TARGETS IN DATABASES

This application claims benefit of Provisional Application Ser. No. 60/357,548 filed Feb. 15, 2002.

BACKGROUND

The present invention relates to methods for identifying hybridization targets of polynucleotide probes within polynucleotide databases. In particular, the present invention provides methods for determining the similarity of polynucleotide probes to polynucleotides in genomic databases, using thermodynamic scoring models.

The rational design of new pharmaceutical agents and therapies is increasingly based on the understanding of disease processes on a cellular and molecular level. For example, through understanding of genetic differences between normal and diseased individuals, differences in the biochemical makeup and function of cells and tissues can be determined and appropriate therapeutic interventions identified.

Accordingly, much effort has been dedicated toward mapping of the human genome, which comprises over $3 \times 10^9$ base pairs of DNA (deoxyribonucleic acid). While this exercise has largely been completed, relatively little is known about which of the estimated 30,000 human genes are specifically involved in any given biochemical process. The analysis of gene function will be a major focus of basic and applied pharmaceutical research over the coming years, toward the end of developing new medicines and therapies for treating a wide variety of disorders. However, the complexity of the human genome and the interrelated functions of many genes make the task exceedingly difficult, and require the development of new analytical tools.

A variety of tools and techniques have already been developed to investigate the structure and function of individual genes and the proteins they express. Such tools include polynucleotide probes, which comprise relatively short, defined sequences of nucleic acids, typically labeled with a radioactive or fluorescent moiety to facilitate detection. Probes may be used in a variety of ways to detect the presence of a polynucleotide sequence, to which the probe binds, in a mixture of genetic material. In general, the target sequence can be harbored by a longer nucleic acid molecule, e.g. a DNA restriction fragment, a PCR (polymerase chain reaction) amplicon, a mRNA (messenger ribonucleic acid) transcript, or a reverse-translated cDNA (complementary DNA) fragment. The detection of the target sequences usually implies the detection of the larger fragment.

Probes may be used as diagnostics, for detection of a particular genetic sequence in genetic material obtained from a subject. The effect of drugs on specific biologic processes (either with respect to efficacy or unwanted side effects) may also be monitored, by using probes to determine the effect of the drug on genes involved in the processes. Probes may also be used in the process of investigating unknown gene functions, such as in gene expression studies, and in genotyping and antisense assays.

The use of probes to monitor changes in gene expression may give insight into the role of specific genes in a given biological process. The amount of mRNA produced by a given gene is related to the involvement of the gene in a given biological process; genes that display an increase of expression activity during the process are likely to be involved in the process. However, correlating the function of any one gene with a biological process is complicated, since most processes are controlled or affected by a large number of genes. Thus, gene expression studies preferably monitor the expression of multiple genes simultaneously.

In order to simultaneously monitor the expression of a large number of genes, high throughput assays have been developed comprising microarrays of probes. Such microarrays comprise a large number of probes of known composition, bound to a substrate. Isolated tissue mRNA is amplified and reverse transcribed to produce cDNA, which is fluorescently labeled. The cDNA is then hybridized to the array, and the level of fluorescence at each probe is detected. The level of fluorescence is proportional to the amount of cDNA bound to the probe and, consequently, to the amount of mRNA in the tissue of interest. The design and application of assays among those known in the art are disclosed in Duggan, D. J., et al., "Expression Profiling Using cDNA Microarrays." *Nature Genetics Supplement* Vol. 21, (1999): 10–14; Roses, D. A. "Pharmacogenetics and the Practice of Medicine." *Nature* Vol. 405, (2000): 857–865; Lockhart, D. J., et al., "Expression Monitoring by Hybridization to High-Density Oligonucleotide Arrays." *Nature Biotechnology* Vol. 14, (1996): 1675–1680; and Lockhart, D. J., and Winzeler, E. A. "Genomics, Gene Expression and DNA Arrays." *Nature* Vol. 405, (2000): 827–836.

The specificity of the probes is essential for the microarray or hybridization-based assays to be meaningful. The utility of a probe to monitor a gene of interest is significantly diminished if it also binds to another gene. This problem is exacerbated when studying large genomes, with commensurately increased possibilities of encountering multiple genes that could bind to a probe that lacks sufficient specificity. Accordingly, a goal of hybridization assay design is to detect only the desired specific target sequence while minimizing interference or cross-hybridization with other polynucleotide sequences present in the polynucleotide mixture being analyzed. Cross-hybridization is typically due to the presence of limited base differences, as well as insertions and deletions within genomic sequences that are similar. The ability to reduce cross-hybridization becomes extremely important when many or all of the sequences present in the complex nucleic acid mixture are previously known, and the number of probes being designed is large (>100).

Insofar as binding of a probe to a polynucleotide target can be characterized according to well-defined rules, probe design can be reduced to a string-matching exercise, which is particularly amenable to computerization. Accordingly, a variety of computerized systems have been developed for analysis of genetic sequences. The use of computers to collect, organize and analyze genetic and protein sequences and associated information is generally known as "bioinformatics." Various types of computer algorithms are described in the literature, such as Myer's grep algorithm, described in Myers, G. "A Fast Bit-Vector Algorithm for Approximate String Matching Based on Dynamic Programming." *Journal of the ACM* Vol. 46, No. 3, (1999): 395–415. However these algorithms only return matches with a given number of mismatches from the query sequence. The mismatch sequences provided by fast algorithms are of initial interest, but fail to include alternate binding sites that contain insertions and deletions that can still cross-hybridize with the selected probe. Thus, approximate string-matching algorithms, although potentially fast, are not very sensitive to detect all alternative binding sites for a probe.

Other common search programs compute an alignment value or "score" for every sequence in the database that matches a given query sequence. The given score for a query sequence represents the degree of similarity between the query sequence and the database sequence. This score is generally calculated from the alignment of the two sequences, and is based on a substitution score matrix. A dynamic programming algorithm for computing the optimal local-alignment score was first described in Smith, T. F. and Waterman, M. S. "Identification of Common Molecular Subsequences." *J. Mol. Biol.* Vol. 147, (1981): 195–197. This dynamic programming algorithm was later improved to include linear gap-penalty functions. Gotoh, O., *J. Mol. Biol.* Vol. 162, (1982): 705–708. Gaps are observed when, in a given alignment, some nucleotides of one sequence have no similar nucleotides in the other sequence. The example below shows an alignment with a gap of two and a gap of one.

```
CTGCCTGTCCCAATGCTC-AGCC          SEQ. ID. NO. 1
|||||||| |||| |||
CTGCCTGTCCC--TGCTCCAGCC          SEQ. ID. NO. 2
```

Gap penalty functions are linear functions of the type:

penalty=initiation+$b$*extension where the term "initiation" is defined as the penalty for gaps of one, the term "extension" is the penalty for any subsequent gap length increase and "b" is the length of the gap minus one.

The similarity scoring scheme used by presently known algorithms works well when the purpose of the search is to look for homologous (i.e. evolutionary related) sequences in the databank. However, the scoring scheme does not translate directly to the strength of the probe binding to detected sites. Thus, these algorithms may fail to identify the binding of probes to sequences that are not homologous, yet exhibit strong binding affinities.

An alternative approach to the current model is to use thermodynamic parameters to score the interaction affinity between a gene probe and potential targets. These approaches evaluate the binding strength of two sequences by computing the sum of the interactions existing within each couple of successive pairs along the sequences. Algorithms and thermodynamic parameters among those known in the art are disclosed in Gray, D. M., and Tinoco, I., Jr. "A New Approach to the Study of Sequence-Dependent Properties of Polynucleotides." *Biopolymers* Vol. 9, (1970): 223–244; SantaLucia, J., Jr. "A Unified View of Polymer, Dumbbell, and Oligonucleotide DNA Nearest-Neighbor Thermodynamics." *Proc. Natl. Acad. Sci. USA* Vol. 95, (1998): 1460–1465; Allawi, H. T. and SantaLucia, J., Jr. "Thermodynamics and NMR of Internal G•T Mismatches in DNA." *Biochemistry* Vol. 36, (1997): 10581–10594; Allawi, H. T. and SantaLucia, J., Jr. "Nearest Neighbor Thermodynamic Parameters for Internal G•A Mismatches in DNA." *Biochemistry* Vol. 37, (1998): 2170–2179; Allawi, H. T. and SantaLucia, J., Jr. "Nearest-Neighbor Thermodynamics of Internal A•C Mismatches in DNA: Sequence Dependence and pH Effects." *Biochemistry* Vol. 37, (1998): 9435–9444; Allawi, H. T. and SantaLucia, J., Jr. "Thermodynamics of Internal C•T Mismatches in DNA." *Nucleic Acids Research* Vol. 26, No. 11, (1998): 2694–2701; Peyret, N., et al., "Nearest-Neighbor Thermodynamics and NMR of DNA Sequences with Internal A•A, C•C, G•G, and T•T Mismatches." *Biochemistry* Vol. 38, (1999): 3468–3477; Peyret, N., and SantaLucia, J., Jr. "Prediction of Nucleic Acid Hybridization: Parameters and Algorithms." *Abstract of Dissertation*, Wayne State University, Detroit, Mich.; Peterson, J. C., et al., "Sequence Information Signal Processor for Local and Global String Comparisons," California Institute of Technology, Pasadena, Calif., USA; U.S. Pat. No. 5,632, 041 (1997); and Kane, M. D., et al., "Assessment of the Sensitivity and Specificity of Oligonucleotide (50 mer) Microarrays." *Nucleic Acids Research* Vol. 28, No. 22, (2000): 4552–4557.

Algorithms among those known in the art evaluate probe/target thermodynamics at every possible point of binding, such as by computationally "walking" the probe along the target, shifting the position of the probe by one nucleotide at each step. Such techniques are extremely computationally demanding, and inefficient. Moreover, many of the algorithms are unable to take into account gaps and other computational exceptions. Database searches using algorithms are also unfortunately quite slow on ordinary computers. Thus, heuristic alternative programs have been developed, such as "FastA" (Fast Alignments), Pearson, W. R., and Lipman, D. J. "Improved Tools for Biological Sequence Comparison." *Proc. Natl. Acad. Sci. USA* Vol. 85, (1988): 2444–2448, and "BLAST" (Basic Local Alignment Search Tool), Altschul, S. F., Madden, T. L., Schäffer, A. A., Zhang, J., Zhang, Z., Miller, W., and Lipman, D. J. "Gapped BLAST and PSI-BLAST: A New Generation of Protein Database Search Programs." *Nucleic Acids Research* Vol. 25, No. 17. (1997): 3389–3402; Altschul, S. F., Gish, W., Miller, W., Myers, E. W., and Lipman, D. J. "Basic Local Alignment Search Tool." *J. Mol. Biol.* Vol. 215, (1990): 403–410.

Although these methods improve the speed of the search by a factor of up to 40 compared with the Smith-Waterman algorithm, they do so at the expense of sensitivity. Due to the loss of sensitivity, some significant "hits" that would indicate alternative binding sites for a probe are not detected using the heuristic algorithms with their standard parameters.

Accordingly, there is a need for an efficient computational method for determining the binding sites of a given probe to a targets in a genome or other composite of polynucleotides. The method should have sufficient sensitivity to find all binding sites of interest, yet process information quickly. Further, the processing method should be designed to be compatible with conventional computer equipment (e.g., readily available personal computers). Such methods preferably take into consideration binding site strength for not only primary binding sequence targets, but alternate sites that include mismatch pairs, insertions, and deletions within the nucleic acid target sequence.

SUMMARY OF THE INVENTION

The present invention provides methods for determining the binding affinity of a probe to a target or targets in a polynucleotide composite using an automated system. Such methods, for the identification of binding sites, or targets, for a polynucleotide probe to individual polynucleotides in a composite using an automated system, comprise the steps of:

a) converting the nucleic acid sequence of said probe to a thermodynamic alphabet sequence using a thermodynamic alphabet; and b) comparing said thermodynamic alphabet sequence of the probe to the thermodynamic alphabet sequence of said individual polynucleotides, using the automated system.

In a preferred embodiment, the present invention provides a method for identifying alternative (secondary) binding sites for a probe in a polynucleotide mixture or database. This invention also provides methods for designing polynucleotide probes for use with a polynucleotide composite comprising a plurality of individual polynucleotides, including a target. Such methods include those comprising the steps of:
- a) selecting an initial probe design;
- b) converting the nucleic acid sequence of said initial probe to a thermodynamic alphabet sequence using a thermodynamic alphabet;
- c) comparing the thermodynamic alphabet sequence of the initial probe to the thermodynamic alphabet sequences of the individual polynucleotides in the composite using an automated system, so as to identify two or more potential target polynucleotides with which the probe may bind;
- d) calculating the binding affinity of the probe to polynucleotides;
- e) comparing the binding affinities of the potential target polynucleotides based on thermodynamic parameters; and
- f) optionally, altering the initial probe to a create a second probe design so as to reduce the number of potential target polynucleotides found by repeating steps a) through e) with respect to the second probe design.

Preferably, the "comparing" step of these methods comprises matching the thermodynamic alphabet word within the thermodynamic alphabet sequence of the probe, ranging from 2 to W letters in length, to the thermodynamic alphabet sequence of the individual polynucleotides in the composite database. The term "W" is defined as a numerical value representing the total length of the nucleic acid sequence. A preferred embodiment of this invention uses a commercially-available sequence comparison program, such as a BLAST program, for performing the comparison.

It has been found that the methods of this invention afford advantages over methods among those known in the art, including one or more of enhanced accuracy, enhanced specificity, increased speed, and increased computational efficiency in probe identification and design. Further advantages and areas of applicability of the present invention will be apparent to one of skill in the art from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Figure 1:
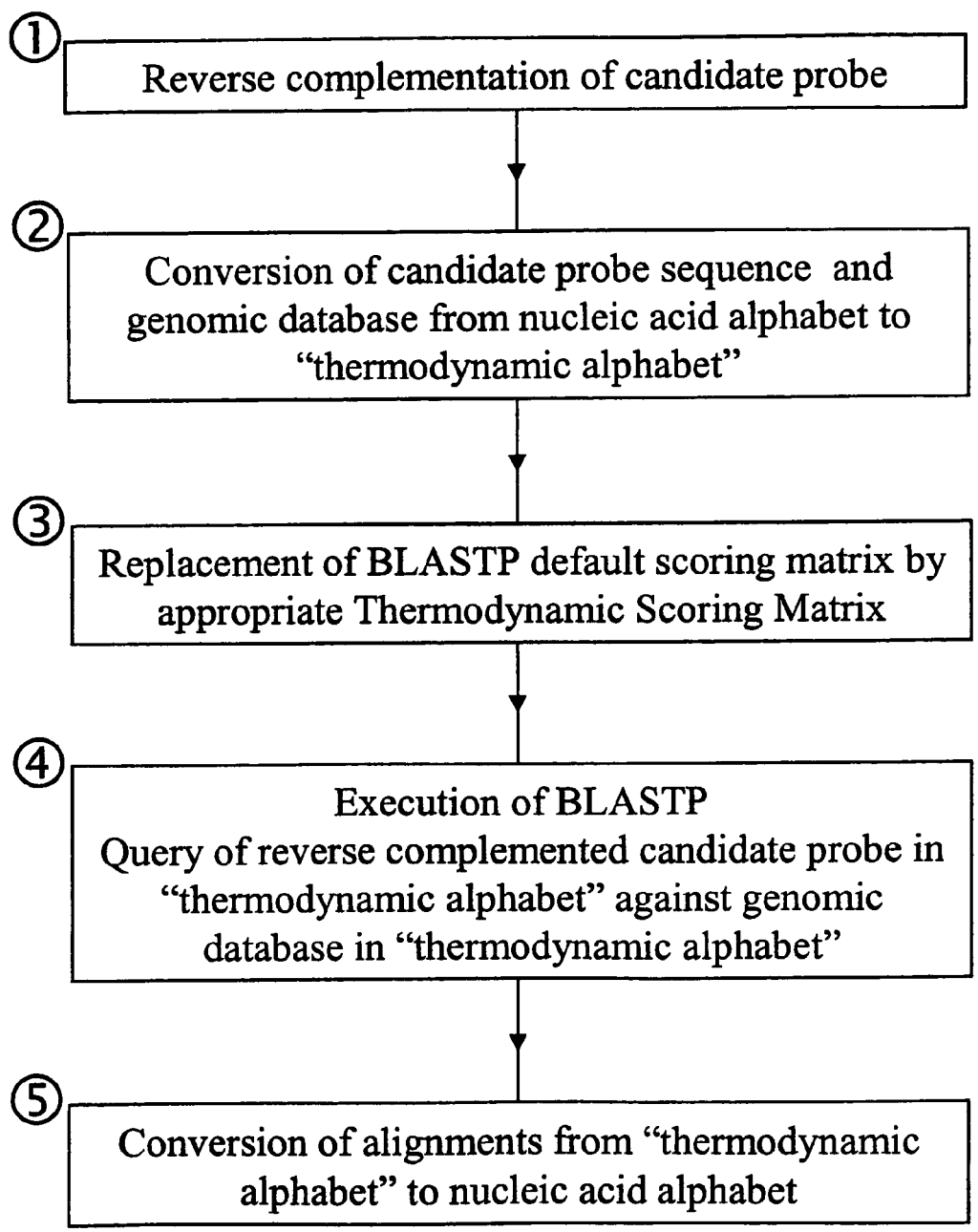
FIG. 1 is a flow chart setting forth the steps in a method of the present invention.
Figure 2:
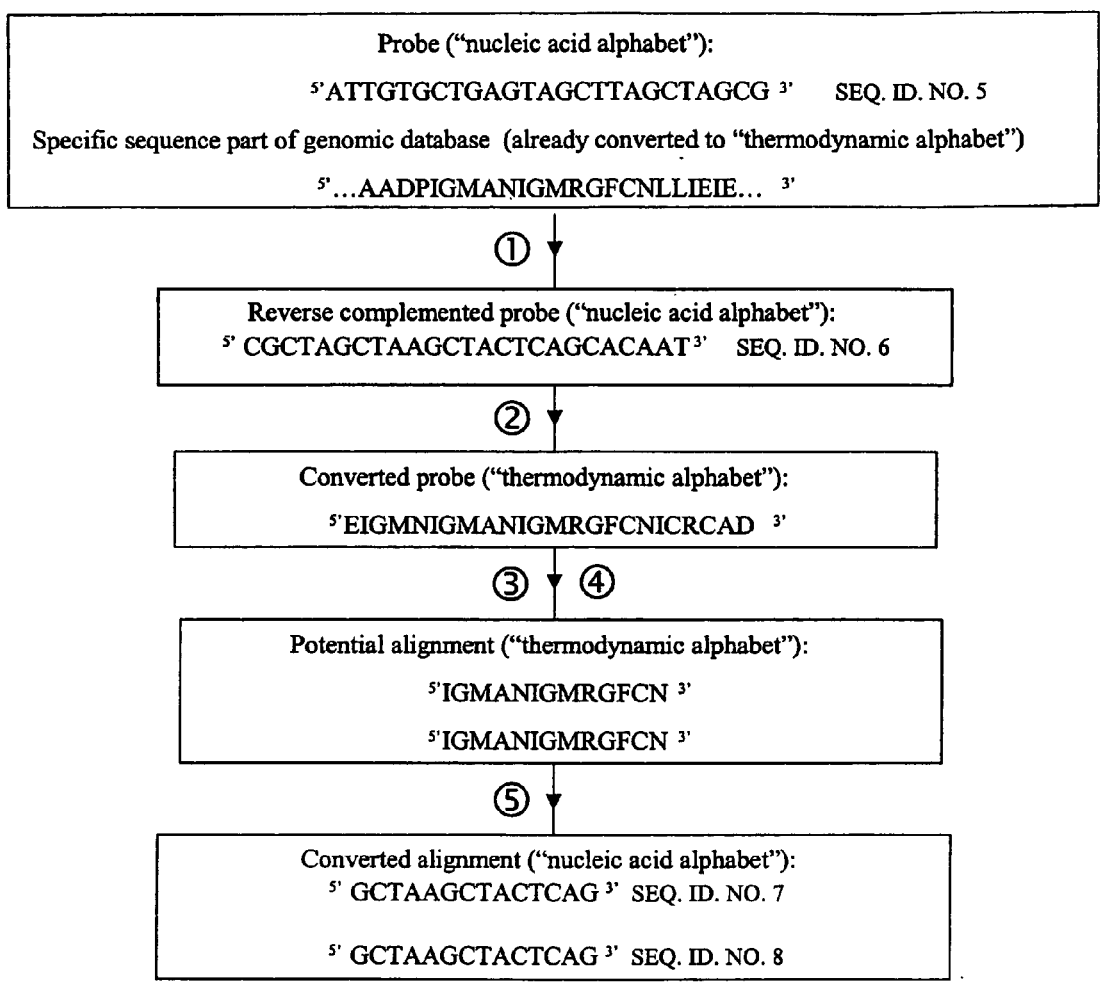
FIG. 2 is an example of the output generated from each step in the process exemplified in FIG. 1.

It should be noted that the plots and figures set forth herein are intended to exemplify the general characteristics of methods among those of this invention, for the purpose of the description of such embodiments herein. These figures may not precisely reflect the characteristics of any given embodiment, and are not necessarily intended to define or limit specific embodiments within the scope of this invention.

DETAILED DESCRIPTION

The present invention provides methods for characterizing the binding potential of a first polynucleotide (a "probe") with one or more other polynucleotides in a polynucleotide mixture, matrix or other composite. As referred to herein, a "polynucleotide" is a nucleotide polymer, comprising two or more nucleotide bases (DNA or RNA) or analogs thereof. Such analogs include peptide nucleic acids (PNA) and locked nucleic acids (LNA). (As used herein, the words "include" and its variants are intended to be non-limiting, such that recitation of items in a list is not to the exclusion of other like items that may also be useful in the materials, compositions, devices, and methods of this invention.)

In one embodiment, the present invention provides methods for determining the specificity of a probe sequence to a target polynucleotide sequence by the use of an automated system. As referred to herein, a "target" is a polynucleotide of interest in a polynucleotide composite. Such targets include those selected using any of a variety of criteria of medical or other research interest. In one embodiment, targets comprise a gene, or genetic fragment having substantial similarity or homology to a gene, preferably such that identification of the target implies the identification of the gene. A "target sequence" is the polynucleotide sequence of a target, in a polynucleotide database.

As referred to herein, a "polynucleotide composite" comprises a plurality of individual polynucleotides. Such composites include physical mixtures of polynucleotides (e.g., genetic material extracted from a cell), mixtures of synthetic polynucleotides, and arrays of natural or synthetic polynucleotides. As referred to herein, a polynucleotide database comprises a plurality of sequences of polynucleotides in a composite. In a preferred embodiment, the database comprises the sequences of a plurality of genes or genetic fragments (a "genetic database"). In one embodiment, the database comprises sequences for more than about 1,000 genes, preferably comprising substantially all of the genes for an organism, e.g., *Homo sapiens*. (As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.)

As referred to herein, a "probe" is a polynucleotide which is of potential interest for binding to a target, and a "probe sequence" is the nucleotide sequence of a probe. The probe may be naturally occurring or synthetic, preferably comprising from about 8 to about 100, more preferably from about 10 to about 70 bases. In a preferred embodiment, the probe is synthetic.

Probe Design:

The design of a hybridization assay relies on the binding of a probe to a target in a polynucleotide composite, e.g., a genome. Specific requirements of probe design will depend on the particular hybridization assay being performed. However, in a preferred embodiment, there are four basic requirements, as follows:

1. Sequence-specific hybridization of the probe with the target sequence;
2. Significant (i.e. detectable) amount of the probe-target hybrid at a given assay temperature;
3. Compatibility with other probes that might be used simultaneously in parallel in the assay (e.g. in a polynucleotide-based microarray sensor); and
4. Minimal cross-hybridization with other sequences in the mixture (i.e. alternate hybridization targets).

In order to comply with the first three general requirements, a number of rules are applied when developing the candidate probe sequences. Such general rules are based on empirically derived methodologies, such as guanine/cytosine composition of the sequence, the specific end nucleotide sequences of the probe, as well as taking into consideration calculations of the probe/target free energy and/or melting temperature.

One of the main difficulties in developing proper hybridization conditions lies in the fourth general requirement that requires minimization of the number of cross-hybridization targets. The present invention provides methods for identifying polynucleotides to which a given polynucleotide, i.e., a probe, will bind in a mixture, array or other composite of polynucleotides. In one embodiment, the present invention provides methods for identifying one or more targets for a probe. In another embodiment, the present invention provides methods for identifying potential alternative binding sites (secondary binding sites or "alternative targets") of the probe that has been designed for a primary target. Such methods, for the identification of potential targets for a probe in a polynucleotide composite by the use of an automated system, comprise the steps of:
 a) converting the nucleic acid sequence of said probe to a thermodynamic alphabet sequence using a thermodynamic alphabet; and
 b) comparing said thermodynamic alphabet sequence of the probe to the thermodynamic alphabet sequence of polynucleotides in said composite, using the automated system.

According to the present invention, the criteria used in scoring or determining the potential targets comprises the free energy values of the probe binding to the targets. The "score" is determined by an algorithmic that uses the nearest-neighbor thermodynamic principle in connection with a thermodynamic scoring matrix, to assign free energy values to each probe/binding site.

Methods of Finding Target Binding Sites for a Probe:

The methods of the present invention can be used in any process where the sequences of polynucleotides in the composite are at least partially known and found in a sequence database. Such methods include the design of DNA probes to target DNA polynucleotides, as well as the design of polynucleotide probes (e.g., DNA, RNA, PNA, DNA, and LNA) to target a specific sequence in any composite of polynucleotide targets. In a preferred embodiment of the present invention, as depicted in FIG. 1, a target sequence in a genomic database and a candidate probe are initially selected. Following the selection of the candidate probe, the probe is reverse complemented (Step 1). The reverse complementation of the candidate probe sequence results in a candidate probe query sequence similar to the original target sequence. Although, in some embodiments, the candidate probe query sequence may not be exactly the same sequence due to length, it is preferably an identical subset of the original target sequence.

Following the reverse complementation of the candidate probe sequence (Step 1), the genomic database and the candidate probe sequence are converted from the nucleic acid alphabet to the "Thermodynamic Alphabet". The nucleic acid sequence and pairing of acid bases correspond to different thermodynamic alphabet parameters (letters) as exemplified in Table 1 below. For DNA polynucleotide embodiments, the probe is converted from its original nucleic acid alphabet sequence (four letters) to a thermodynamic alphabet (16 letters) sequence. In a preferred embodiment, this thermodynamic alphabet is based on the nearest-neighbor principles, as described in Gray, D. M., and Tinoco, I., Jr. "A New Approach to the Study of Sequence-Dependent Properties of Polynucleotides." *Biopolymers* Vol. 9, (1970): 223–244; and SantaLucia, J., Jr. "A Unified View of Polymer, Dumbbell, and Oligonucleotide DNA Nearest-Neighbor Thermodynamics." *Proc. Natl. Acad. Sci. USA* Vol. 95, (1998): 1460–1465, under the assumption of equilibrium. For instance, in the case of DNA, the 16-letter alphabet corresponds to the following nearest neighbors in the nucleotide alphabet: AA, AC, AG, AT, CA, CC, CG, CT, GA, GC, GG, GT, TA, TC, TG, TT.

TABLE 1

Correspondence between the "Thermodynamic Alphabet" and the nucleotide alphabet.

| "Thermodynamic Alphabet" | Nucleotide Alphabet |
|---|---|
| A | AA |
| R | AC |
| N | AG |
| D | AT |
| C | CA |
| Q | CC |
| E | CG |
| G | CT |
| H | GA |
| I | GC |
| L | GG |
| K | GT |
| M | TA |
| F | TC |
| P | TG |
| S | TT |

After the conversion of the candidate probe sequence and the genomic database to the "Thermodynamic Alphabet," the converted sequences are input into an algorithm that is designed to detect relationships among sequences which share only isolated regions of similarity. The automated systems for use in the methods of this invention include any of a variety of computer programs among those known in the art for analysis of nucleotide or peptide sequences executing such algorithms. Such computer programs preferably have the capability of processing large genomic databases and specific sequences from the original nucleic acid sequences using a designated "alphabet". In the present invention, the sequences are converted to a thermodynamic based alphabet for determining binding affinity.

In a preferred embodiment, the algorithm comprises a similarity search program of the type known in the art as the BLAST (Basic Local Alignment Search Tool), which is designed to explore all of the available sequence databases regardless of whether the query is a protein or a polynucleotide. BLAST is currently the most widely used program for fast database searches. Although variations are useful, two different versions of the program are preferred: one for comparing nucleic acid sequences (BLASTN) and one for comparing protein sequences (BLASTP). BLASTN uses an alphabet of four bases whereas BLASTP uses an alphabet of 20 amino acids. The outputs of the programs are nucleic acid or protein sequence alignments. These alignments are scored and ranked according to the sequence similarity for nucleic acids (the unitary scoring matrix) or using evolutionary models (e.g. PAM and BLOSUM series of amino-acid substitution scoring matrices) in the case of proteins. In other embodiments, this invention can be used in conjunction with sequence comparison algorithms such as Smith-Waterman and FastA. Using the Smith-Waterman algorithm the sensitivity is provided at the expense of computation speed, but through the use of hardware accelerators, or with SIMD implementations of the algorithm, this limitation can be easily overcome.

The BLASTP program is a particularly preferred algorithm. Although the BLASTP search program is originally designed for protein sequences, the present invention provides a nearest-neighbor based thermodynamic alphabet sequence as the input sequence and reference sequence for the BLASTP program. In a preferred embodiment, the comparison of the probe segments to the target sequence is performed using thermodynamic nearest-neighbor principles.

In one embodiment, the nearest-neighbor model pioneered by Tinoco et al. considers that the thermodynamic properties (enthalpy, entropy, and free energy) of an polynucleotide sequence can be expressed as the sum of elementary increments made of two adjacent base pairs or nearest neighbors. This model assumes that the thermodynamic properties of duplex formation are a function of both the base pair content as well as the stacking orientation of adjacent (i.e. neighboring) base pairs. For instance, according to the nearest-neighbor model, the thermodynamics of formation of the internal section:

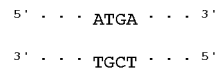

is the sum of individual contributions of adjacent base pairs, namely

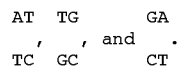

There are 16 possible Watson-Click nearest neighbors, as shown in Table 1. However, when each strand of a duplex is constituted by the same nucleic acid (DNA/DNA or RNA/RNA) this number is reduced to 10 because of symmetry reasons. For instance

is equivalent to

The value of the elementary increments is experimentally determined by measuring the thermodynamic properties of a set of polynucleotides by UV thermo-melting, and extracting the elementary contributions of the nearest neighbors by multiple linear regressions.

As can be seen in Tables 2 through 8, different thermodynamic parameters, including free energy parameters ($\Delta G°_{37}$), exist between different nucleic acid base pairing. Also, in the case of DNA, the nearest-neighbor model applies not only to canonical Watson-Crick duplexes but also to sequences with single internal mismatches. Elementary increments for all the sus-cited systems are available. The model may also be applied to other systems, such as DNA/PNA and DNA/LNA duplexes. The following tables exemplify the various thermodynamic parameters:

TABLE 2

Nearest-neighbor thermodynamic parameters for Watson-Crick duplex formation in 1 M NaCl, pH 7 (Allawi, H. T. and SantaLucia, J., Jr. (1997) Biochemistry, 36, 10581–10594).

| Propagation sequence | $\Delta H°$ (kcal mol$^{-1}$) | $\Delta S°$ (cal mol$^{-1}$ K$^{-1}$) | $\Delta G°_{37}$ (kcal mol$^{-1}$) |
|---|---|---|---|
| AA/TT | −7.9 ± 0.2 | −22.2 ± 0.8 | −1.00 ± 0.01 |
| AT/TA | −7.2 ± 0.7 | −20.4 ± 2.4 | −0.88 ± 0.04 |
| TA/AT | −7.2 ± 0.9 | −21.3 ± 2.4 | −0.58 ± 0.06 |
| CA/GT | −8.5 ± 0.6 | −22.7 ± 2.0 | −1.45 ± 0.06 |
| GT/CA | −8.4 ± 0.5 | −22.4 ± 2.0 | −1.44 ± 0.04 |
| CT/GA | −7.8 ± 0.6 | −21.0 ± 2.0 | −1.28 ± 0.03 |
| GA/CT | −8.2 ± 0.6 | −22.2 ± 1.7 | −1.30 ± 0.03 |
| CG/GC | −10.6 ± 0.6 | −27.2 ± 2.6 | −2.17 ± 0.05 |
| GC/CG | −9.8 ± 0.4 | −24.4 ± 2.0 | −2.24 ± 0.03 |
| GG/CC | −8.0 ± 0.9 | −19.9 ± 1.8 | −1.84 ± 0.04 |
| Initiation with terminal G-C | 0.1 ± 1.1 | −2.8 ± 0.2 | 0.98 ± 0.05 |
| Initiation with terminal A-T | 2.3 ± 1.3 | 4.1 ± 0.2 | 1.03 ± 0.05 |
| Symmetry correction | 0 | −1.4 | 0.3 |

TABLE 3

Thermodynamic parameters for internal A · C mismatches in 1 M NaCl (Allawi, H. T., and SantaLucia, J., Jr. (1998) Biochemistry, 37, 9435–9444). These sequences represent a complete set of linearly independent nearest-neighbor trimers.

| Propagation sequence | pH | $\Delta H°$ (kcal mol$^{-1}$) | $\Delta S°$ (cal mol$^{-1}$ K$^{-1}$) | $\Delta G°_{37}$ (kcal mol$^{-1}$) |
|---|---|---|---|---|
| ACC/TAG | 7 | 10.5 ± 1.4 | 28.8 ± 3.0 | 1.58 ± 0.09 |
|  | 5 | −9.6 ± 1.9 | −30.6 ± 2.7 | −0.12 ± 0.12 |
| CCC/GAG | 7 | 5.8 ± 1.6 | 13.5 ± 2.7 | 1.60 ± 0.13 |
|  | 5 | −4.6 ± 1.5 | −15.3 ± 2.5 | 0.13 ± 0.11 |
| GCA/CAT | 7 | 2.7 ± 1.5 | 4.2 ± 2.7 | 1.39 ± 0.15 |
|  | 5 | −7.0 ± 1.3 | −22.3 ± 2.7 | −0.07 ± 0.14 |
| GCC/CAG | 7 | 4.5 ± 1.4 | 10.4 ± 2.7 | 1.28 ± 0.13 |
|  | 5 | −8.2 ± 1.2 | −25.1 ± 2.9 | −0.43 ± 0.14 |
| GCC/CAC | 7 | 1.2 ± 1.4 | −0.1 ± 2.0 | 1.22 ± 0.15 |
|  | 5 | −9.1 ± 1.8 | −28.3 ± 2.7 | −0.31 ± 0.13 |
| GCT/CAA | 7 | 1.6 ± 1.2 | 0.8 ± 2.8 | 1.35 ± 0.13 |
|  | 5 | −5.7 ± 1.1 | −18.6 ± 2.4 | 0.06 ± 0.12 |
| TCC/AAG | 7 | 12.8 ± 1.6 | 34.4 ± 2.8 | 2.14 ± 0.15 |
|  | 5 | −1.1 ± 1.2 | −5.5 ± 2.1 | 0.60 ± 0.11 |

TABLE 4

Thermodynamic parameters for internal C · T mismatches in 1 M NaCl pH 7 (Allawi, H. T., and SantaLucia, J., Jr. (1998) Nucleic Acids Res., 26, 2694–2701). These sequences represent a complete set of linearly independent nearest-neighbor trimers.

| Propagation sequence | $\Delta H°$ (kcal mol$^{-1}$) | $\Delta S°$ (cal mol$^{-1}$ K$^{-1}$) | $\Delta G°_{37}$ (kcal mol$^{-1}$) |
|---|---|---|---|
| ACC/TTG | 5.9 ± 1.3 | 13.8 ± 2.6 | 1.62 ± 0.10 |
| CCC/GTG | 4.4 ± 1.2 | 9.0 ± 2.5 | 1.60 ± 0.13 |
| GCA/CTT | 3.3 ± 1.1 | 6.2 ± 2.2 | 1.37 ± 0.12 |
| GCC/CTG | 7.5 ± 1.5 | 19.0 ± 3.0 | 1.60 ± 0.13 |
| GCG/CTC | 0.8 ± 1.2 | −0.7 ± 2.5 | 1.02 ± 0.11 |
| GCT/CTA | 1.1 ± 1.3 | −0.8 ± 2.0 | 1.35 ± 0.12 |
| TCC/ATG | 6.4 ± 1.3 | 14.3 ± 2.9 | 1.95 ± 0.14 |

TABLE 5

Thermodynamic parameters for internal G · A mismatches in 1 M NaCl, pH 7 (Allawi, H. T. and SantaLucia, J., Jr. (1998) Biochemistry, 37, 2170–2179). These sequences represent a complete set of linearly independent nearest-neighbor trimers.

| Propagation sequence | $\Delta H°$ (kcal mol$^{-1}$) | $\Delta S°$ (cal mol$^{-1}$ K$^{-1}$) | $\Delta G°_{37}$ (kcal mol$^{-1}$) |
|---|---|---|---|
| AAC/TGG | −0.1 ± 1.5 | 0.9 ± 3.2 | −0.38 ± 0.11 |
| CAC/GGG | −0.2 ± 1.1 | 0.9 ± 3.2 | −0.49 ± 0.12 |
| GAA/CGT | 2.5 ± 1.7 | 6.5 ± 3.5 | 0.49 ± 0.09 |
| GAC/CGG | −0.1 ± 1.7 | 2.2 ± 2.9 | −0.78 ± 0.11 |
| GAG/CGC | −4.6 ± 1.6 | −14.4 ± 3.0 | −0.14 ± 0.10 |
| GAT/CGA | −1.2 ± 2.0 | −3.1 ± 3.8 | −0.24 ± 0.14 |
| TAC/AGG | 1.1 ± 1.9 | 3.9 ± 2.9 | −0.10 ± 0.10 |

TABLE 6

Thermodynamic parameters for internal G·T mismatches in 1 M NaCl, pH 7 (Allawi, H. T. and SantaLucia, J., Jr. (1997) Biochemistry, 36, 10581–10594). These sequences represent a complete set of linearly independent nearest-neighbor trimers.

| Propagation sequence | $\Delta H°$ (kcal mol$^{-1}$) | $\Delta S°$ (cal mol$^{-1}$ K$^{-1}$) | $\Delta G°_{37}$ (kcal mol$^{-1}$) |
|---|---|---|---|
| AGC/TTG | −3.4 ± 1.6 | −11.4 ± 5.0 | 0.12 ± 0.15 |
| ATC/TGG | 0.6 ± 1.8 | 1.6 ± 2.9 | 0.15 ± 0.14 |
| CGC/GTG | −8.6 ± 1.4 | −24.3 ± 4.5 | −1.05 ± 0.10 |
| CTC/GGG | 0.4 ± 1.1 | −2.2 ± 3.3 | −0.24 ± 0.13 |
| GTC/CGG | −1.2 ± 1.3 | −2.4 ± 3.9 | −0.51 ± 0.08 |
| TGC/ATG | −4.5 ± 1.0 | −14.1 ± 3.4 | −0.16 ± 0.12 |
| TTC/AGG | 1.9 ± 1.5 | 4.9 ± 3.5 | 0.42 ± 0.15 |

TABLE 7

Nearest-neighbor thermodynamic parameters for Watson-Crick RNA duplex formation in 1 M NaCl, pH 7 (Xia, T., SantaLucia, Jr., J., Burkard, M. E., Kierzek, R., Schroeder, S. J., Jiao, X., Cox, C., and Turner, D. H. (1998) Biochemistry, 37, 14719–14735).

| Propagation sequence | $\Delta H°$ (kcal mol$^{-1}$) | $\Delta S°$ (cal mol$^{-1}$ K$^{-1}$) | $\Delta G°_{37}$ (kcal mol$^{-1}$) |
|---|---|---|---|
| AA/UU | −6.8 ± 0.8 | −19.0 ± 2.5 | −0.93 ± 0.03 |
| AU/UA | −9.4 ± 1.7 | −26.7 ± 5.2 | −1.10 ± 0.08 |
| UA/AU | −7.7 ± 2.0 | −20.5 ± 6.3 | −1.33 ± 0.09 |
| CA/GU | −10.4 ± 1.3 | −26.9 ± 3.9 | −2.11 ± 0.07 |
| GU/CA | −11.4 ± 1.23 | −29.5 ± 3.9 | −2.24 ± 0.06 |
| CU/GA | −10.5 ± 1.2 | −27.1 ± 3.8 | −2.08 ± 0.06 |
| GA/CU | −12.4 ± 1.2 | −32.5 ± 3.7 | −2.35 ± 0.06 |
| CG/GC | −10.6 ± 1.7 | −26.7 ± 5.0 | −2.36 ± 0.09 |
| GC/CG | −14.9 ± 1.6 | −36.9 ± 4.9 | −3.42 ± 0.08 |
| GG/CC | −13.4 ± 1.2 | −32.7 ± 3.8 | −3.26 ± 0.07 |
| Initiation | 3.61 ± 4.12 | −1.5 ± 12.7 | 4.09 ± 0.22 |
| Terminal A-U | 3.72 ± 0.83 | 10.5 ± 2.6 | 0.45 ± 0.04 |
| Symmetry correction | 0 | −1.4 | 0.43 |

TABLE 8

Linearly independent Nearest-neighbor Thermodynamic Parameters for A · A, C · C, G · G and T · T mismatch formation in 1 M NaCl, pH 7 (N. Peyret, P. A. Seneviratne, H. T. Allawi, and J. SantaLucia, Jr. (1999) Biochemistry 38, 3468–3477).

| Propagation Sequence | $\Delta H°$ (kcal/mol) | $\Delta S°$ (eu) | $\Delta G°_{37}$ (kcal/mol) |
|---|---|---|---|
| A · A mismatches | | | |
| AA/TA | 1.2 ± 2.5 | 1.7 ± 8.0 | 0.61 ± 0.13 |
| CA/GA | −0.9 ± 2.3 | −4.2 ± 7.3 | 0.43 ± 0.17 |
| GA/CA | −2.9 ± 4.1 | −9.8 ± 13.1 | 0.17 ± 0.23 |
| TA/AA | 4.7 ± 2.4 | 12.9 ± 7.7 | 0.69 ± 0.05 |

TABLE 8-continued

Linearly independent Nearest-neighbor Thermodynamic Parameters for
A · A, C · C, G · G and T · T mismatch formation in 1 M NaCl, pH 7
(N. Peyret, P. A. Seneviratne, H. T. Allawi, and J. SantaLucia, Jr.
(1999) Biochemistry 38, 3468–3477).

| Propagation Sequence | ΔH° (kcal/mol) | ΔS° (eu) | ΔG°$_{37}$ (kcal/mol) |
|---|---|---|---|
| C · C mismatches | | | |
| A<u>C</u>/T<u>C</u> | 0.0 ± 2.1 | −4.4 ± 6.5 | 1.33 ± 0.09 |
| C<u>C</u>/G<u>C</u> | −1.5 ± 1.1 | −7.2 ± 4.7 | 0.70 ± 0.05 |
| G<u>C</u>/<u>C</u>C | 3.6 ± 3.2 | 8.9 ± 9.8 | 0.79 ± 0.09 |
| T<u>C</u>/A<u>C</u> | 6.1 ± 1.1 | 16.4 ± 3.5 | 1.05 ± 0.06 |
| G · G mismatches | | | |
| A<u>G</u>/T<u>G</u> | −3.1 ± 1.3 | −9.5 ± 4.0 | −0.13 ± 0.09 |
| C<u>G</u>/<u>G</u>G | −4.9 ± 1.1 | −15.3 ± 3.3 | −0.11 ± 0.11 |
| G<u>G</u>/C<u>G</u> | −6.0 ± 2.5 | −15.8 ± 7.8 | −1.11 ± 0.13 |
| T<u>G</u>/A<u>G</u> | 1.6 ± 0.8 | 3.6 ± 2.5 | 0.44 ± 0.14 |
| T · T mismatches | | | |
| A<u>T</u>/T<u>T</u> | −2.7 ± 4.1 | −10.8 ± 13.1 | 0.69 ± 0.23 |
| C<u>T</u>/G<u>T</u> | −5.0 ± 1.4 | −15.8 ± 13.9 | −0.12 ± 0.23 |
| G<u>T</u>/C<u>T</u> | −2.2 ± 1.1 | −8.4 ± 3.2 | 0.45 ± 0.05 |
| T<u>T</u>/A<u>T</u> | 0.2 ± 1.8 | −1.5 ± 5.8 | 0.68 ± 0.08 |

Extra significant figures are given to allow accurate calculation of the T$_M$ and ΔG°$_{37}$. Underlined residues are mismatched. Errors are resampling standard deviations.
These parameters should not be used to calculate the stability of oligonucleotides with mismatches in the terminal or penultimate positions.

In order to convert the similarity search program (e.g., BLASTP) to one that will process nucleic acid sequences converted to the thermodynamic alphabet, a thermodynamic scoring matrix, is used to replace the original amino-acid substitution matrices commonly used with the program (e.g., Step 3 in FIG. 1). Various matrixes may be used during the execution of the program, such as a 4 by 4 matrix, a 16 by 16 matrix based on the nearest-neighbor principles.

One embodiment of a scoring matrix, set forth in Table 9, contains the free-energy scores of the nearest neighbors corresponding to all the possible DNA/DNA alignments.

the first row and first column represent the "Thermodynamic Alphabet" as shown in Table 1. Each letter corresponds to the nearest-neighbor dinucleotide of the Thermodynamic Alphabet. In general, the matrix contains the free-energy scores of the nearest neighbors corresponding to all the possible alignments. Various Thermodynamic Scoring Matrices specific for RNA, RNA/DNA, RNA/PNA, DNA/PNA, or DNA/LNA hybrids can also be calculated from empirical thermodynamic data and modified for assay conditions if the parameters and rules are available.

In one embodiment, the nearest-neighbor free-energy increments used in the scoring matrix is calculated to reflect different experimental conditions. These include assay temperature, monovalent cation concentration, magnesium concentration, and concentrations of other additives such as urea or DMSO that affect the equilibrium thermodynamics. For instance, to modify the scoring matrix to account for assay temperature, the free energy parameters are recalculated using the following equation:

$$\text{Equation 1:} \quad \Delta G_T^o = \Delta H^o + T \times \frac{\Delta G_{37}^o - \Delta H^o}{310.15}$$

where ΔG°$_{37}$ and ΔH° are parameters available in the literature and T is the temperature of the assay. Also, to take into account the effect of monovalent cations on DNA/DNA hybridization, the following equation can be used to rescale the 1M Na$^+$ salt parameters in the scoring matrix to the concentration [Na$^+$]:

$$\text{Equation 2:} \quad \Delta G_{37}^{o[Na^+]} = \Delta G_{37}^{o1M} - 0.114 \times \ln[Na^+]$$

where ΔG°$_{37}$$^{[Na^+]}$ is the free energy for the assay performed in a sodium concentration [Na$^+$], and ΔG°$_{37}$$^{1M}$ is the free energy (available in the literature) for the assay performed in 1M sodium concentration, as shown in Table 9. See, San-

TABLE 9

Thermodynamic Scoring Matrix, 1 M Na+

| | A | R | N | D | C | Q | E | G | H | I | L | K | M | F | P | S | T | ... |
|---|---|---|---|---|---|---|---|---|---|---|---|---|---|---|---|---|---|---|
| A | 10 | −6 | −7 | −7 | −8 | −10 | −10 | −10 | −3 | −10 | −10 | −10 | −7 | −10 | −10 | −10 | 0 | |
| R | −1 | 14 | 1 | −1 | −10 | −10 | −10 | −10 | −10 | 6 | −10 | −10 | −10 | −5 | −10 | −10 | 0 | |
| N | −9 | −13 | 13 | −7 | −10 | −10 | −4 | −10 | −10 | −10 | 3 | −10 | −10 | −10 | 1 | −10 | 0 | |
| D | −6 | −8 | 0 | 9 | −10 | −10 | −10 | −10 | −7 | −10 | −10 | −1 | −10 | −10 | −10 | −7 | 0 | |
| C | −7 | −10 | −10 | −10 | 15 | −6 | 5 | 1 | −4 | −10 | −10 | −10 | −4 | −10 | −10 | −10 | 0 | |
| Q | −10 | 5 | −10 | −10 | 0 | 18 | 1 | 3 | −10 | 11 | −10 | −10 | −10 | −1 | −10 | −10 | 0 | |
| E | −10 | −10 | −1 | −10 | −8 | −7 | 22 | −4 | −10 | −10 | 1 | −10 | −10 | −10 | 5 | −10 | 0 | |
| G | −10 | −10 | −10 | 0 | −4 | −8 | −1 | 13 | −10 | 1 | −10 | −10 | −10 | −10 | −7 | −10 | 0 | |
| H | −13 | −10 | −10 | −10 | −11 | −10 | −10 | −10 | 13 | −6 | −1 | −5 | −10 | −10 | −10 | −10 | 0 | |
| I | −10 | −5 | −10 | −10 | −10 | −8 | −10 | −10 | 3 | 22 | 11 | 6 | −10 | −6 | −10 | −10 | 0 | |
| L | −10 | −10 | −8 | −10 | −10 | −10 | −7 | −10 | −8 | −8 | 18 | −10 | −10 | −10 | −6 | −10 | 0 | |
| K | −10 | −10 | −10 | −8 | −10 | −10 | −10 | −13 | −2 | −5 | 5 | 14 | −10 | −10 | −10 | −6 | 0 | |
| M | −7 | −10 | −10 | −10 | −9 | −10 | −10 | −10 | −4 | −10 | −10 | 6 | −10 | −4 | −7 | 0 | | |
| F | −10 | −2 | −10 | −10 | −10 | −8 | −10 | −10 | 3 | −10 | −10 | −4 | 13 | −4 | −3 | 0 | | |
| P | −10 | −10 | −4 | −10 | −10 | −10 | −8 | −10 | −10 | −10 | 0 | −10 | −9 | −11 | 15 | −8 | 0 | |
| S | −10 | −10 | −10 | −6 | −10 | −10 | −10 | −9 | −10 | −10 | −10 | −1 | −7 | −13 | −7 | 10 | 0 | |
| T | 0 | 0 | 0 | 0 | 0 | 0 | 0 | 0 | 0 | 0 | 0 | 0 | 0 | 0 | 0 | 0 | 0 | |
| ... | | | | | | | | | | | | | | | | | | |

The particular Thermodynamic Scoring Matrix of Table 9 is scaled according to experimental parameters for an assay performed in 1M Na$^+$ at 37 degrees Celsius. The letters in taLucia, J., Jr. "A Unified View of Polymer, Dumbbell, and Oligonucleotide DNA Nearest-Neighbor Thermodynamics." Proc. Natl. Acad. Sci. USA, 95: 1460–1465 (1998).

Table 10 is another embodiment of a scoring matrix, scaled for a hybridization assay performed in 0.1 M Na+ at 37 degrees Celsius. The values for the matrix of Table 10 are derived from the scoring matrix in Table 9 by scaling the numbers using Equation 2, wherein [Na+] is equal to 0.1 M.

Based on the alphabet order given in Table 9, the second diagonal entry of the matrix (R, R) corresponds to AC aligned with AC. As the query is reverse complemented for the search, this alignment corresponds to the probe/target nearest neighbor AC/TG, which has a free energy contribu-

TABLE 10

Thermodynamic Scoring Matrix, 0.1 M Na+

| | A | R | N | D | C | Q | E | G | H | I | L | K | M | F | P | S | T | ... |
|---|---|---|---|---|---|---|---|---|---|---|---|---|---|---|---|---|---|---|
| A | 7 | −9 | −10 | −10 | −10 | −13 | −13 | −13 | −6 | −13 | −13 | −13 | −9 | −13 | −13 | −13 | 0 | |
| R | −4 | 12 | −1 | −3 | −13 | −12 | −13 | −13 | −13 | 3 | −13 | −13 | −13 | −7 | −13 | −13 | 0 | |
| N | −11 | −16 | 10 | −10 | −13 | −13 | −7 | −13 | −13 | −13 | 1 | −13 | −13 | −13 | −1 | −13 | 0 | |
| D | −9 | −10 | −3 | 6 | −13 | −13 | −13 | −10 | −13 | −13 | −13 | −3 | −13 | −13 | −13 | −10 | 0 | |
| C | −10 | −13 | −13 | −13 | 12 | −9 | 2 | −1 | −7 | −13 | −13 | −13 | −7 | −13 | −13 | −13 | 0 | |
| Q | −13 | 3 | −13 | −13 | −3 | 16 | −2 | 1 | −13 | 8 | −13 | −13 | −13 | −3 | −13 | −13 | 0 | |
| E | −13 | −13 | −4 | −13 | −10 | −10 | 19 | −7 | −13 | −13 | −2 | −13 | −13 | −13 | 2 | −13 | 0 | |
| G | −13 | −13 | −13 | −3 | −7 | −11 | −4 | 10 | −13 | −13 | −13 | −1 | −13 | −13 | −13 | −10 | 0 | |
| H | −16 | −13 | −13 | −13 | −13 | −13 | −13 | −13 | 10 | −9 | −3 | −7 | −12 | −13 | −13 | −13 | 0 | |
| I | −13 | −7 | −13 | −13 | −13 | −11 | −13 | −13 | 0 | 20 | 8 | 3 | −13 | −9 | −13 | −13 | 0 | |
| L | −13 | −13 | −11 | −13 | −13 | −13 | −10 | −13 | −11 | −11 | 16 | −12 | −13 | −13 | −9 | −13 | 0 | |
| K | −13 | −13 | −13 | −10 | −13 | −13 | −13 | −16 | −4 | −7 | 3 | 12 | −13 | −13 | −13 | −9 | 0 | |
| M | −10 | −13 | −13 | −13 | −13 | −12 | −13 | −13 | −7 | −13 | −13 | −13 | 3 | −12 | −7 | −9 | 0 | |
| F | −13 | −4 | −13 | −13 | −13 | −11 | −13 | −13 | −13 | 0 | −13 | −13 | −7 | 10 | −7 | −6 | 0 | |
| P | −13 | −13 | −7 | −13 | −13 | −13 | −10 | −13 | −13 | −13 | −3 | −13 | −12 | −13 | 12 | −10 | 0 | |
| S | −13 | −13 | −13 | −9 | −13 | −13 | −13 | −11 | −13 | −13 | −13 | −4 | −10 | −16 | −10 | 7 | 0 | |
| T | 0 | 0 | 0 | 0 | 0 | 0 | 0 | 0 | 0 | 0 | 0 | 0 | 0 | 0 | 0 | 0 | 0 | |
| ... | | | | | | | | | | | | | | | | | | |

These nearest-neighbor free-energy scores of the thermodynamic scoring matrixes, as exemplified in Tables 9 and 10, are directly proportional to the nearest-neighbor free-energy increments expressed in kcal/mol. A proportionality constant allows easy conversion of the scores to the real free energies as shown in Equation 3, wherein k=−10 mol/kcal. Therefore, the nearest-neighbor score value present in Equation 3 below, is the value present in the thermodynamic scoring matrix being used.

nearest-neighbor free-energy increment=k×nearest-neighbor score          Equation 3

The nearest-neighbor free-energy increments are determined based on the genomic database sequences and the original probe sequences in question. In one embodiment, the BLASTP program is run with the transposed sequences and using the Thermodynamic Matrix as the scoring matrix, producing a list of alignments that correspond to alternative binding sites (Si) (written in the nearest-neighbor alphabet) and scores that are directly related to the thermodynamic free energy of the probe binding to the alternative sites (e.g., Step 4 in FIG. 1). The execution of the BLASTP program processes the query of the reverse complemented candidate probe against the genomic database, both of which are configured in the "Thermodynamic Alphabet". The BLASTP word size is preferably set to W=2, in order to enhance sensitivity. The word size (W) is the minimum length of a high scoring segment pair required for this initial segment to be extended by dynamic programming. Although 2 is a preferred word size, other word sizes may be used.

Following the execution of the BLASTP program, the alignments are converted back to the standard nucleic acid alphabet (e.g., Step 5 in FIG. 1). This conversion is preferably executed by an additional program, for the ease of inspection. Upon reviewing the program output, the alternate binding sites can be determined based on the free energy increments and the data output of the BLASTP program.

tion of −1.4 kcal/mol (known from the literature). The number reported in the matrix is 14, otherwise obtained by using Equation 3, wherein the nearest-neighbor free-energy increment is:

"k×nearest-neighbor score" or "−10 mol/kcal×−1.4 kcal/mol"

Likewise, diagonal elements (represented in bold) in the matrix, Table 9, are scores for the Watson-Crick nearest neighbors and non diagonal elements are scores for nearest neighbors with single or double mismatches.

The present invention also provides methods for determining the specificity of binding of a polynucleotide probe to a polynucleotide target in a polynucleotide composite comprising said target and a plurality of other individual polynucleotides, using an automated system, said method comprising the steps of:

a) converting the nucleic acid sequence of said probe to a thermodynamic alphabet sequence using a thermodynamic alphabet;

b) comparing said thermodynamic alphabet sequence of the probe to the thermodynamic alphabet sequence of said target and said other individual polynucleotides in said composite, using said automated system, so as to find one or more other potential alternative targets to which said probe may bind;

c) calculating the binding affinities of said probe to said target and to said potential alternative targets;

d) comparing the binding affinities of said probe said potential alternative targets.

Use of Thermodynamic Data to Score Specificity:

In a preferred embodiment, probe specificity is ultimately determined by how much of the total signal generated by a probe is not caused by its intended target (i.e. best hit, highest scoring alignment) but instead by a spurious, alternative target (e.g. second best hit, second highest scoring alignment). Probes can either be in excess (microarrays, genotyping assays) or default compared to the targets. The following specificity ratio describes the specificity of a given probe in some given conditions and can be used to rank probes in terms of specificity.

Equation 4: $$R_s = \frac{Fb(\text{best hit}) \times C(\text{best hit}) - Fb(\text{2nd best hit}) \times C(\text{2nd best hit})}{Fb(\text{best hit}) \times C(\text{best hit})}$$

Where Fb(best hit) and C(best hit) are the fraction hybridized and initial concentration of the probe's intended target, and Fb(2nd best hit) and C(2nd best hit) are the fraction hybridized and initial concentration of the most stable spurious target. Fraction of target hybridized can be calculated from the free energy, or BLASTP scores, and the target and probe initial concentrations.

Equation 4 can be generalized to:

Equation 5: $$R_s = \frac{Fb(\text{best hit}) \times C(\text{best hit}) - \sum_i [Fb(i^{th}\text{ best hit}) \times C(i^{th}\text{ best hit})]}{Fb(\text{best hit}) \times C(\text{best hit})}$$

Where Fb(best hit) and C(best hit) are the fraction hybridized and initial concentration of the probe's intended target and $Fb(i^{th}$ best hit) and $C(i^{th}$ best hit) are the fraction hybridized and initial concentration of the $i^{th}$ best hit. When targets are in excess compared to the probes, fraction hybridized have to be calculated considering the competition between the targets.

This invention also provides methods for designing probes, identifying probes having greatest binding selectivity for a given primary target, i.e., reduced cross-hybridization to other polynucleotides. Such methods include those comprising the steps of:
  a) selecting an initial candidate probe;
  b) converting the nucleic acid sequence of said probe to a thermodynamic alphabet sequence using a thermodynamic alphabet;
  c) comparing said thermodynamic alphabet sequence of said initial probe to the thermodynamic alphabet sequence of said primary target and other polynucleotides in said composite, using an automated system, so as to identify one or more alternative targets with which said probe may bind;
  d) calculating the binding affinities of said probe to said primary target and to said alternative targets;
  e) comparing the binding affinities of said primary target and said alternative targets; and
  f) altering said initial probe design to a create a second probe design having reduced binding affinity to other polynucleotides by repeating steps a) through e) with respect to said second probe design.

In one embodiment, the initial probe may be selected by design of the probe using appropriate criteria given the nature of the primary target and hybridization assay conditions. In another embodiment, the initial probe may be selected randomly from a mixture of polynucleotides, or selected from a mixture of polynucleotides by appropriate criteria.

In one embodiment, the method of this invention said altering step is repeated until a probe is selected having minimal binding affinity to other polynucleotides in the composite. In one embodiment, the multiple repetition of steps a) through e) is sequential, such that a additional probe designs are not selected until preceding probe designs are subjected to steps b) through e). In another embodiment, the multiple repetition of steps a) through e) is substantially concurrent, such that multiple probes are evaluated simultaneously, and a probe having the minimum binding affinity to other polynucleotides is identified.

The following are non-limiting Examples of the methods of this invention.

EXAMPLE 1

In order to fully understand the benefit of using the BLASTP program based on the thermodynamic alphabet, a comparison with BLASTN using a standard alphabet and scoring matrix, is provided below. Typically, sequence alignments containing stable mismatches get low ranking with BLASTN. For example, the alignment:

```
CTGCCTGTCCCAATGCTC-AGCCC        SEQ. ID. NO. 3
|||||||| |||| |||
CTGCCTGTCCCTCTGCTCCGGCCC        SEQ. ID. NO. 4
``` is assigned a score of 78 by BLASTN (barely above a very relaxed scoring cutoff of 75) using a standard scoring matrix and set of gap penalties. The same alignment using the thermodynamic BLASTP scoring matrix gets a score of 254, which ranks it in the top ten scoring alignments (and well above a comparable scoring cutoff of 200). The estimated stability of −25.4 kcal/mol is great enough to cause this mismatch to interfere with hybridization, yet might have been missed entirely by a less than exhaustive BLASTN search. The speed and sensitivity of BLASTP using the thermodynamic matrix and alphabet is comparable to that of BLASTN with a word size W=4, and the resulting ranking of alignments more accurately reflects the likelihood of hybridization between two sequences.

EXAMPLE 2

Specific probes against *Saccharomyces cerevisiae's* genes are designed using a method of this invention. Specifically, *Saccharomyces cerevisiae's* genome (including mitochondrial DNA) and gene sequences (ORF) are obtained from the Stanford *Saccharomyces* Genome Database. See, Cherry, J. M., et al., *Saccharomyces* Genome Database, available at genome-www.stanford.edu/Saccharomyces (Oct. 7, 2002); and Cherry, J. M., et al, SGD: *Saccharomyces* Genome Database. Nucleic Acids Res., 26, 73–80. (1998). *Saccharomyces cerevisiae's* genome and mitochondrial DNA are reverse complemented, and both original and reverse complement of the genome are converted to thermodynamic alphabet to create a database for searching with WU-BLAST. See, Gish, W.), available at blast.wustl.edu (1996–2002).

As an example source of probes, a random ORF sequence (YIR022W) with 505 nucleotides is sampled, starting at every base, to yield 481 and 446 probe sequences of 25 and 60 bases, respectively. The nucleotide sequences of the probes are translated into the corresponding thermodynamic alphabet.

Probes are then blasted against the database using both BLASTP with thermodynamic scoring matrix of Table 9 as well as BLASTN with default matrix. Separate genome screens are performed for each set of 25-mer and 60-mer probes using each of the two scoring matrices. For DNA probe sequences, BLASTN is used with a word size of 5. For the thermodynamic alphabet sequences, BLASTP is used with the thermodynamic matrix and gap penalties Q=26 R=13. For each search, the top 10 scoring alignments for each query are used for analysis. The thermodynamic alphabet sequences are first reverse translated into DNA sequences then folded to yield approximate free energy values of hybridization. See, Ivo Hofacker. Institut für theoretische Chemie, Währingerstr. 17, A-1090 Wien, Austria. available at www.tbi.univie.ac.at/~ivo/RNA/.

Figure 3:
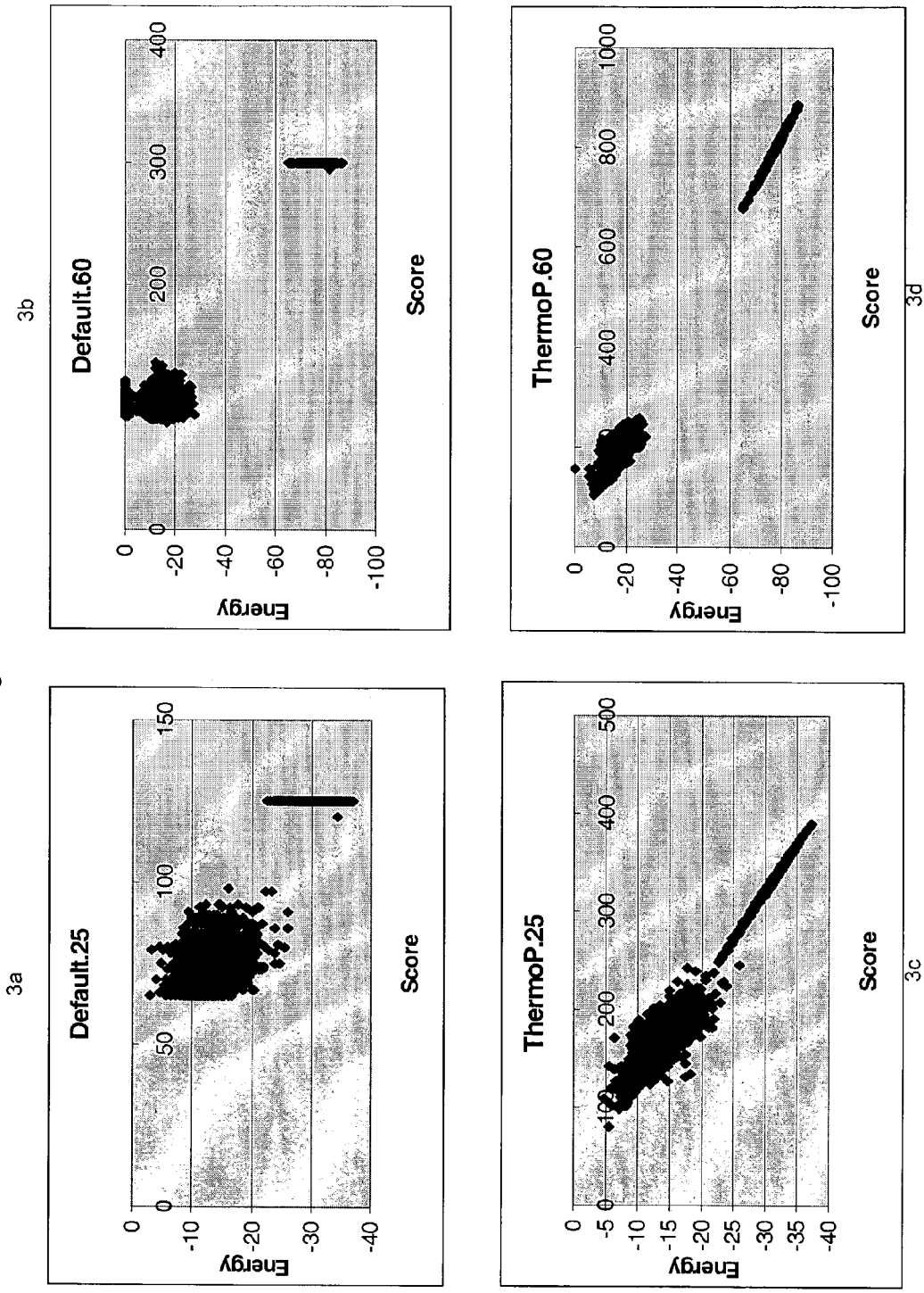
FIG. 3 depicts plots showing the relationship between alignment free energy and BLAST scoring for an exemplary method of this invention and a method of the art.
Figure 4:
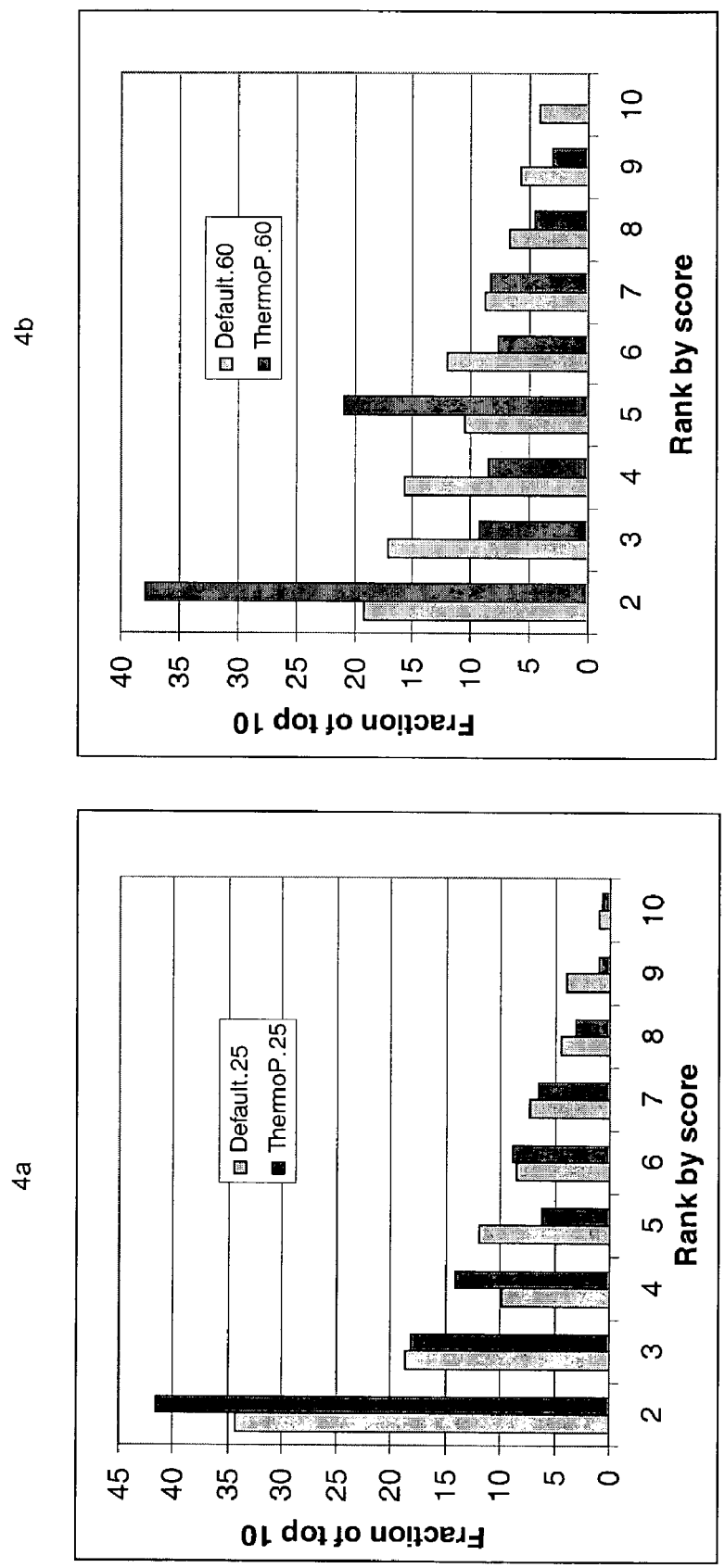
FIG. 4 depicts plots showing the ranking of alignment by energy scores for probes identified using an exemplary method of this invention and a method of the art.

Exemplary relationships between calculated hybridization energies and BLAST scores obtained with the different search matrices are shown in FIG. 3. The best correlation is obtained with BLASTP using the thermodynamic matrix. Ranking of the "second-best" most energetically favorable alignment by score is shown in FIG. 4. In this example, the BLASTP with thermodynamic matrix scores perform best, especially for the 60-mer case. With the aim of minimizing potential sources of cross hybridization for DNA probes, use of the nearest-neighbor encoding thermodynamic scoring matrix in conjunction with BLASTP shows the best correlation between screening score and energy.

The examples and other embodiments described herein are exemplary and not intended to be limiting in describing the full scope of the methods of this invention. Equivalent changes, modifications and variations of specific embodiments, materials, compositions and methods may be made within the scope of the present invention, with substantially similar results.

What is claimed is:

1. A method for identifying polynucleotides to which a probe may bind in a composite of individual polynucleotides, using an automated system, comprising the steps of:
   a) converting the nucleic acid sequence of said probe to a thermodynamic alphabet sequence using a thermodynamic alphabet;
   b) comparing said thermodynamic alphabet sequence of said probe to the thermodynamic alphabet sequences of individual polynucleotides in said composite, using said automated system.

2. A method according to claim 1 wherein said comparing step is performed using a pre-defined matrix containing thermodynamic parameter values.

3. A method according to claim 2 wherein said matrix is a 4 by 4 matrix, 16 by 16 matrix, or a 64 by 64 matrix.

4. A method according to claim 3 wherein said matrix is a 4 by 4 matrix or a 16 by 16 matrix.

5. A method according to claim 4 wherein said matrix is a 16 by 16 matrix.

6. A method according to claim 1 wherein said comparing step comprises matching of thermodynamic alphabet words within said thermodynamic alphabet sequence of said probe to said thermodynamic alphabet sequences of said individual polynucleotides.

7. A method according to claim 6 wherein said word size is from 2 to 10 letters in length.

8. A method according to claim 7 wherein said word size is from 2 to 4 letters in length.

9. A method according to claim 8 wherein said word size is 2 letters in length.

10. A method according to claim 6 wherein said automated system is a BLAST program.

11. A method according to claim 10 wherein said BLAST program is BLASTP.

12. A method according to claim 1, additionally comprising the step, after said comparing step, of calculating the binding affinity of the probe to individual polynucleotides with which the probe may bind.

13. A method according to claim 12, additionally comprising the step, after said calculating step, of comparing the relative binding affinities of said individual polynucleotides based on thermodynamic parameters.

14. A method according to claim 13, wherein said step of comparing relative binding affinities comprises calculating the specificity of binding of said probe to said individual polynucleotides using the formula $$R_s = \frac{Fb(\text{best hit}) \times C(\text{best hit}) - \sum_i [Fb(i^{th} \text{ best hit}) \times C(i^{th} \text{ best hit})]}{Fb(\text{best hit}) \times C(\text{best hit})}.$$

15. A method according to claim 12, additionally comprising the step, after said step of comparing relative binding affinities, of converting the thermodynamic alphabet of said individual polynucleotides to the nucleic acid sequence of said polynucleotides.

16. A method for determining the specificity of binding of a polynucleotide probe to a polynucleotide target in a polynucleotide composite comprising said target and a plurality of other individual polynucleotides, using an automated system, said method comprising the steps of:
   a) converting the nucleic acid sequence of said probe to a thermodynamic alphabet sequence using a thermodynamic alphabet;
   b) comparing said thermodynamic alphabet sequence of said probe to the thermodynamic alphabet sequence of said target and said other individual polynucleotides in said composite, using said automated system, so as to find one or more other potential alternative targets to which said probe may bind;
   c) calculating the binding affinities of said probe to said target and to said potential alternative targets;
   d) comparing the binding affinities of said target and said potential alternative targets.

17. A method according to claim 16 wherein said comparing step is performed using a pre-defined matrix containing thermodynamic parameter values.

18. A method according to claim 17 wherein said matrix is a 16 by 16 matrix.

19. A method according to claim 16 wherein said comparing step (b) comprises matching of thermodynamic alphabet words, of from 2 to 4 letters in length, within said thermodynamic alphabet sequence of said probe to said thermodynamic alphabet sequences of said other polynucleotides.

20. A method according to claim 16 wherein said automated system is a BLASTP program.

21. A method according to claim 16, wherein said comparing step (d) comprises calculating the specificity of binding of said probe to said potential alternative targets using the formula $$R_s = \frac{Fb(\text{best hit}) \times C(\text{best hit}) - \sum_i [Fb(i^{th} \text{ best hit}) \times C(i^{th} \text{ best hit})]}{Fb(\text{best hit}) \times C(\text{best hit})}.$$

22. A method for designing a polynucleotide probe for a polynucleotide target, said probe having reduced cross-hybridization potential to other polynucleotides in a polynucleotide composite comprising said target and other polynucleotides, comprising the steps of:
   a) selecting an initial probe;
   b) converting the nucleic acid sequence of said initial probe to a thermodynamic alphabet sequence using a thermodynamic alphabet;
   c) comparing said thermodynamic alphabet sequence of said initial probe to the thermodynamic alphabet sequence of said target and said other polynucleotides in said composite, using an automated system, so as to identify one or more of potential alternative targets with which said probe may bind;

d) calculating the binding affinities of said probe to said target and to said potential alternative targets;

e) comparing the binding affinities of said target and said potential alternative targets; and f) altering said initial probe design to a create a second probe design having a reduced binding affinity to other polynucleotides by repeating steps a) through e) with respect to said second probe design.

23. A method according to claim 22 wherein said comparing step (c) is performed using a pre-defined matrix containing thermodynamic parameter values.

24. A method according to claim 23 wherein said matrix is a 16 by 16 matrix.

25. A method according to claim 22 wherein said comparing step (c) comprises matching of thermodynamic alphabet words, of from 2 to 4 letters in length, within said thermodynamic alphabet sequence of said probe to said thermodynamic alphabet sequences of said individual polynucleotides.

26. A method according to claim 22 wherein said automated system is a BLASTP program.

27. A method according to claim 22, wherein said comparing step (e) comprises calculating the specificity of binding of said probe to said potential alternative targets using the formula $$R_s = \frac{Fb(\text{best hit}) \times C(\text{best hit}) - \sum_i [Fb(i^{th} \text{ best hit}) \times C(i^{th} \text{ best hit})]}{Fb(\text{best hit}) \times C(\text{best hit})}.$$

* * * * *

UNITED STATES PATENT AND TRADEMARK OFFICE
CERTIFICATE OF CORRECTION

PATENT NO. : 7,085,652 B2  Page 1 of 1
APPLICATION NO. : 10/366977
DATED : August 1, 2006
INVENTOR(S) : Charles R. Scafe et al.

It is certified that error appears in the above-identified patent and that said Letters Patent is hereby corrected as shown below:

Title Page: Inventor name: Delete "Scaf" and insert --Scafe-- under(12) United States Patent and (75) Inventors.

Title Page: Under (56) References Cited, Peterson, J.C. et al. reference, after U.S. insert --Patent-- and before Appl.

Col. 4, Line 39: Delete "a" after "to"

Col. 5, Line 21: Delete "a" after "to"

Col. 9, Line 50: Delete "Click" and insert --Crick--

Col. 16, Line 57: Insert --to-- after "probe"

Col. 18, Line 2: Delete "a" after "that"

Col. 25, Line 9: Delete "a" after "to"

Signed and Sealed this

Fifth Day of December, 2006

JON W. DUDAS
*Director of the United States Patent and Trademark Office*